United States Patent [19]

Fuchs et al.

[11] 4,326,087
[45] Apr. 20, 1982

[54] 3-BROMO-4-FLUORO-BENZYL DERIVATIVES

[75] Inventors: Rainer Fuchs; Fritz Maurer, both of Wuppertal; Uwe Priesnitz, Unna-Massen; Hans-Jochem Riebel, Wuppertal; Erich Klauke, Odenthal, all of Fed. Rep. of Germany

[73] Assignee: Bayer Aktiengesellschaft, Leverkusen, Fed. Rep. of Germany

[21] Appl. No.: 173,544

[22] Filed: Jul. 30, 1980

[30] Foreign Application Priority Data

Aug. 22, 1979 [DE] Fed. Rep. of Germany ....... 2933985

[51] Int. Cl.³ .............................................. C07C 43/21
[52] U.S. Cl. .................................... 568/631; 568/661; 568/812; 568/639; 570/127
[58] Field of Search ............... 568/812, 639, 647, 661, 568/631; 570/127

[56] References Cited

U.S. PATENT DOCUMENTS

| | | | |
|---|---|---|---|
| 2,073,010 | 3/1937 | Holt | 568/647 |
| 2,109,514 | 5/1937 | Van Zuzec et al. | 568/647 X |
| 2,121,723 | 7/1937 | Bass et al. | 568/647 X |
| 2,121,724 | 7/1937 | Bass et al. | 568/647 X |

FOREIGN PATENT DOCUMENTS

| | | | |
|---|---|---|---|
| 3380 | 8/1979 | European Pat. Off. | 568/639 |
| 8734 | 8/1979 | European Pat. Off. | 568/639 |
| 50-85986 | 3/1975 | Japan | 568/661 |
| 2010837 | 7/1979 | United Kingdom | 568/639 |

*Primary Examiner*—Bernard Helfin
*Attorney, Agent, or Firm*—Sprung, Felfe, Horn, Lynch & Kramer

[57] ABSTRACT

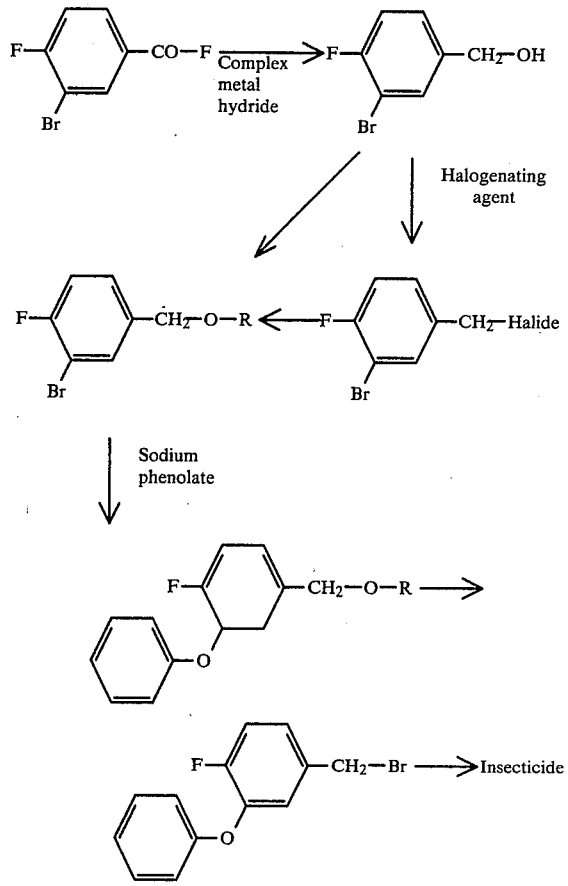

7 Claims, No Drawings

3-BROMO-4-FLUORO-BENZYL DERIVATIVES

The invention relates to certain new 4-fluoro-3-phenoxybenzyl ethers, to a process for their preparation, to new 3-bromo-4-fluorobenzyl ethers and 3-bromo-4-fluorobenzyl halides and 3-bromo-4-fluorobenzyl alcohol as intermediate products for this process and to processes for their preparation.

It is known that 4-fluoro-3-phenoxy-benzyl bromide, an intermediate product for pesticidally active pyrethroids, is obtained when 4-fluoro-3-phenoxy-toluene is reacted with N-bromosuccinimide in carbon tetrachloride using azodiisobutyric acid nitrile as the catalyst (see U.S. Pat. No. 4,218,469 issued Aug. 19, 1980. However, because of the high cost of the reagents and because of the unsatisfactory yields, this synthesis method is not very suitable for the preparation of 4-fluoro-3-phenoxybenzyl bromide on an industrial scale.

The present invention now provides:
(1), as new compounds, the 4-fluoro-3-phenoxy-benzyl ethers of the general formula

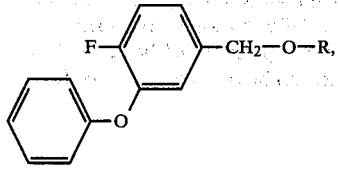

in which R represents phenyl or benzyl;
(2) a process for the preparation of a compound of the formula (I), characterized in that a 3-bromo-4-fluoro-benzyl ether of the general formula

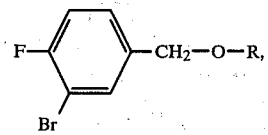

in which R has the meaning indicated above, is reacted with an alkali metal phenolate or alkaline earth metal phenolate, if appropriate in the presence of an auxiliary selected from alkali metal halides and carbonates and alkaline earth metal halides and carbonates, and in the presence of copper or a copper compound as a catalyst, and using a diluent, at a temperature between about 100° and 200° C.;
(3) the use of the new compounds of the formula (I) as intermediate products for the preparation of 4-fluoro-3-phenoxy-benzyl bromide by reaction with hydrogen bromide by known methods for splitting ethers;
(4), as new compounds, the 3-bromo-4-fluoro-benzyl ethers of the general formula

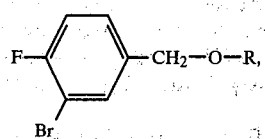

in which R represents phenyl or benzyl;
(5) a process for the preparation of 3-bromo-4-fluoro-benzyl phenyl ether (II, R=phenyl), characterized in that a 3-bromo-4-fluoro-benzyl halide of the general formula

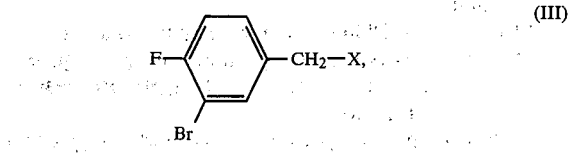

in which X represents chlorine or bromine, is reacted with an alkali metal phenolate or alkaline earth metal phenolate, if appropriate in the presence of a diluent, at a temperature between about 0° and 150° C.;
(6) a process for the preparation of 3-bromo-4-fluoro-benzyl benzyl ether (II, R=benzyl), characterized in that 3-bromo-4-fluoro-benzyl alcohol, of the formula

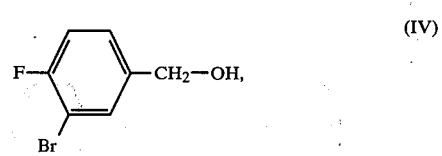

is reacted with a benzyl halide in the presence of a base and if appropriate using a diluent, at a temperature between about 0° and 150° C.;
(7), as new compounds, the 3-bromo-4-fluoro-benzyl halides of the general formula

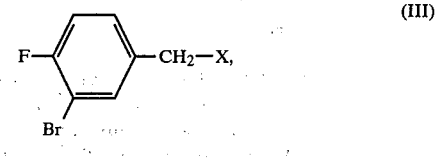

in which X represents chlorine or bromine;
(8) a process for the preparation of a 3-bromo-4-fluoro-benzyl halide of the formula (III), characterized in that 3-bromo-4-fluoro-benzyl alcohol of the formula (IV) above is reacted with a halogenating agent, if appropriate using a diluent, at a temperature between about −10° and 100° C.;
(9), as a new compound, 3-bromo-4-fluoro-benzyl alcohol, of the formula

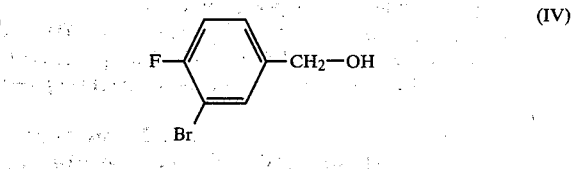

and
(10) a process for the preparation of 3-bromo-4-fluoro-benzyl alcohol of the formula (IV) above, characterized in that 3-bromo-4-fluoro-benzyl fluoride, of the formula

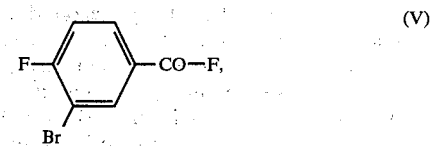

is reacted with a complex hydride of the formula
 M(M'H$_4$) (VI), in which

M represents lithium, sodium or potassium and

M' represents boron or aluminum, is appropriate in the presence of a diluent, at a temperature between about 0° and 50° C.

4-Fluoro-3-phenoxy-benzyl bromide can be prepared with the aid of the new 4-fluoro-3-phenoxy-benzyl ethers of the formula (I) in a considerably more simple manner than by the above-mentioned known process.

If 4-fluoro-3-bromo-benzyl benzyl ether and potassium phenolate are used as starting substances, the process described under (2) ("process (2)") can be outlined by the following equation:

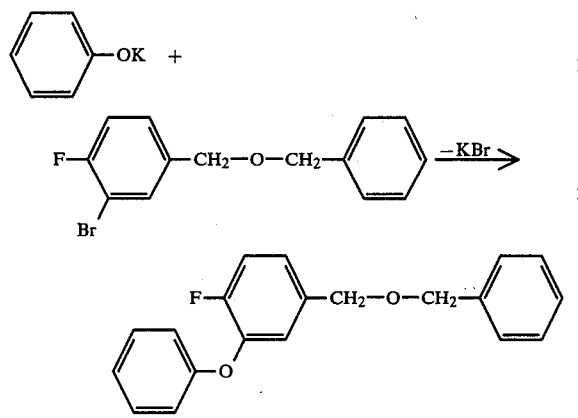

Alkali metal phenolates or alkaline earth metal phenolates which can be used as starting substances in process (2) are, for example, sodium phenolate, potassium phenolate and magnesium phenolate. Sodium phenolate is the preferred starting compound. Auxiliaries from the series comprising alkali metal halides or carbonates and alkaline earth metal halides or carbonates are, for example, potassium chloride and magnesium chloride, and potassium carbonate and magnesium carbonate. These auxiliaries are preferably used if sodium phenolate is employed as the starting compound.

Copper or copper compounds are used as the catalysts. Examples of these catalysts which may be mentioned are copper, copper(I) oxide, copper(II) oxide, copper(I) chloride and copper(I) bromide.

The reaction temperature is kept between 100° and 200° C., preferably about 140° to 180° C., in process (2). The process is usually carried out under normal pressure.

About 1 to 1.5 mols, preferably 1 to 1.2 mols, of phenolate, if appropriate 10 to 200 g of an auxiliary from the series comprising alkali metal halides or carbonates and alkaline earth metal halides or carbonates and 0.01 to 0.5 mol, preferably 0.1 to 0.5 mol, of copper catalyst are employed per mol of 3-bromo-4-fluorobenzyl ether of the formula (II).

In a preferred variant (a) a process (2) for the preparation of 4-fluoro-3-phenoxy-benzyl benzyl ether, isoquinoline is used as the diluent. For carrying out process variant (2)(a), the components are mixed and the mixture is heated, while stirring, until the reaction has ended. Working up can be carried out in the customary manner. For example, the reaction mixture is diluted, after cooling, with a water-immiscible solvent, for example cyclohexane, and filtered, the filtrate is washed with hydrochloric acid and water, dried and filtered and the solvent is distilled off from the filtrate. The crude product which remains can be purified by vacuum distillation.

In a further preferred variant (b) of process (2) for the preparation of 4-fluoro-3-phenoxy-benzyl phenyl ether, bis-(2-methoxyethyl) ether (diglyme) is used as the diluent. For carrying out process variant (2)(b), the components are mixed and the mixture is heated, while stirring, until the reaction has ended. Working up can be carried out in the customary manner. For example, the reaction mixture is diluted, after cooling, with a water-immiscible solvent, for example toluene, and filtered, the filtrate is washed with dilute sodium hydroxide solution and with water, dried and filtered and the solvent is distilled off from the filtrate. The crude product which remains can be purified by vacuum distillation.

The new compounds of the formula (I) can be used as intermediate products for the preparation of 4-fluoro-3-phenoxy-benzyl bromide, which is known as an intermediate product for pyrethroids (see DE-OS (German Published Specification) No. 2,709,264).

If 4-fluoro-3-phenoxy-benzyl benzyl ether is used, the preparation of 4-fluoro-3-phenoxy-benzyl bromide by splitting ether compounds of the formula (I) with hydrobromic acid can be illustrated by the following equation:

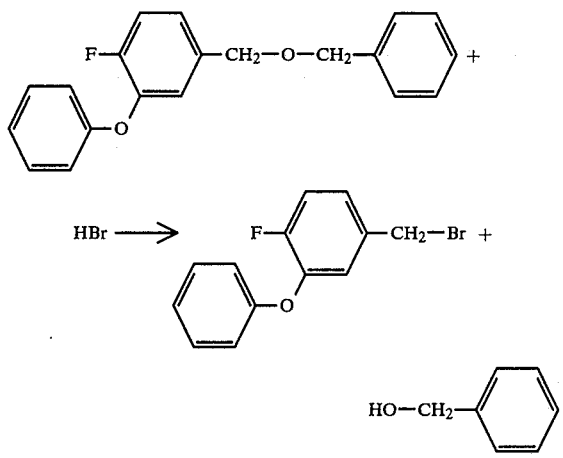

The splitting of the ether for the preparation of 4-fluoro-3-phenoxy-benzyl bromide can be carried out by customary methods.

In a preferred procedure, the selected compound of the formula (I) is heated with aqueous hydrobromic acid and acetic acid under reflux for several hours. For working up, the reaction mixture is diluted, if appropriate, with water, and extracted with a water-immiscible solvent, for example methylene chloride. The extracts are washed with dilute sodium hydroxide solution and dried. The solvent is then carefully distilled off under reduced pressure and the crude product, which remains as the residue, is purified, if appropriate, by vacuum distillation.

If 3-bromo-4-fluoro-benzyl chloride and potassium phenolate are used as starting substances, the process described under (5) for the preparation of 3-bromo-4-fluoro-benzyl phenyl ether ("process (5)") can be outlined by the following equation:

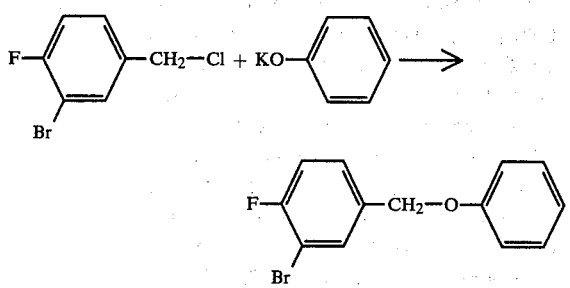

Alkali metal phenolates or alkaline earth metal phenolates which can be used as starting substances in process (5) are, for example, sodium phenolate, potassium phenolate and magnesium phenolate. Sodium phenolate is the preferred starting compound.

Process (5) is preferably carried out using a diluent. Preferred diluents are aprotic polar solvents, for example tetrahydrofuran, glycol dimethyl ether, acetonitrile, dimethylformamide or dimethylsulphoxide.

The reaction temperature is kept between 0° and 150° C., preferably about 10° to 100° C., in process (5). The process is in general carried out under normal pressure.

About 1 to 1.5 mols, preferably 1 to 1.2 mols, of phenolate are employed per mol of 3-bromo-4-fluorobenzyl halide (III).

In a preferred embodiment of process (5), the phenolate is initially introduced in a diluent and the 3-bromo-4-fluoro-benzyl halide is added dropwise, while stirring. The reaction mixture is then stirred, if appropriate at moderately elevated temperature, until the reaction has ended. Working up can be carried out in the customary manner, for example by diluting the mixture with water and extracting it with a water-immiscible solvent, for example methylene chloride, drying and filtering the extracts, concentrating the filtrate and distilling the residue, if appropriate in vacuo.

If benzyl bromide is used as the reaction component, the process described under (6) for the preparation of 3-bromo-4-fluoro-benzyl benzyl ether ("process (6)") can be outlined by the following equation:

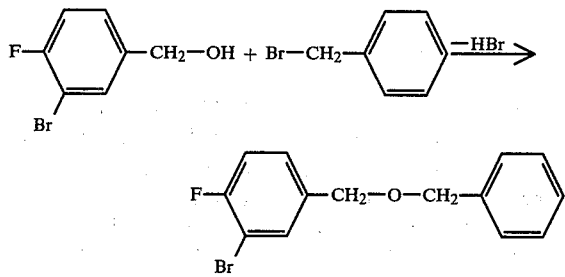

Process (6) is preferably carried out using a diluent. The same solvents as in process (5) are preferred.

Benzyl halides which are preferably employed in process (6) are benzyl chloride and benzyl bromide.

Bases suitable for deprotonating benzyl alcohols are used in process (6). Possible bases of this type are alcoholates, for example sodium methylate and potassium tert.-butylate, alkali metal amides, for example sodium amide, and alkali metal hydrides, for example sodium hydride.

The reaction temperature is kept between 0° and 150° C., preferably about 10° to 100° C., in process (6). The process is in general carried out under normal pressure.

About 1 to 1.5 mols, preferably 1 to 1.2 mols, of base and 1 to 1.5 mols, preferably 1 to 1.2 mols, of benzyl halide are employed per mol of 3-bromo-4-fluoro-benzyl alcohol.

In a preferred embodiment of process (6), the base is initially introduced in a diluent and 3-bromo-4-fluoro-benzyl alcohol is added. After about one hour, the benzyl halide is added dropwise to this mixture, and the mixture is stirred, if appropriate at moderately elevated temperature, until the reaction has ended. Working up can be carried out in the customary manner, for example by adding dilute hydrochloric acid to the reaction mixture, extracting the mixture with a water-immiscible solvent, for example diethyl ether, drying and filtering the ether extract and distilling the filtrate.

The process for the preparation of 3-bromo-4-fluoro-benzyl halides from 3-bromo-4-fluoro-benzyl alcohol ("process (8)") is preferably carried out using a diluent. Preferred diluents are aliphatic and aromatic, optionally halogenated hydrocarbons, for example pentane, hexane, heptane, cyclohexane, petroleum ether, ligroin, benzene, toluene, xylene, methylene chloride, ethylene chloride, chloroform, carbon tetrachloride, chlorobenzene and o-dichlorobenzene.

Halogenating agents to be used in process (8) are, for example, thionyl chloride, phosphorus trichloride, phosphorus pentachloride, phosphorus tribromide and dibromo-triphenyl-phosphorane.

The reaction temperature is between −10° and 100° C., preferably about 0° to 50° C., in process (8). The process is in general carried out under normal pressure.

For carrying out process (8), 3-bromo-4-fluorobenzyl alcohol is initially introduced, if appropriate in one of the diluents indicated above, and at least the equivalent amount of a halogenating agent is added dropwise. When the reaction has ended, the product can be isolated in the pure form by distillation. Another form of working up consists in diluting the reaction mixture with water, separating off, drying and filtering the organic phase and distilling the filtrate.

The process for the preparation of 3-bromo-4-fluoro-benzyl alcohol ("process (10)") is preferably carried out using a diluent. Preferred diluents are alcohols, for example methanol, ethanol, n- and iso-propanol and n-, iso-, sec.- and tert.-butanol. Iso-propanol is the particularly preferred diluent.

Complex hydrides of the formula (VI) to be used as reducing agents in process (10) are, for example, lithium tetrahydridoaluminate (lithium alanate) and sodium tetrahydridoborate (sodium boranate). The latter is particularly preferred.

Process (10) is carried out at a temperature between 0° and 50° C., preferably about 10° to 40° C., and usually under normal pressure.

In a preferred embodiment of process (10), the complex hydride of the formula (VI) is initially introduced in one of the diluents indicated above, and 3-bromo-4-fluoro-benzoyl fluoride is slowly added dropwise. The reaction mixture is stirred until the reaction has ended and is diluted with ice-water and acidified. It is then extracted with a water-immiscible solvent, for example methylene chloride, the extract is dried and filtered and the filtrate is distilled.

The 3-bromo-4-fluoro-benzoyl fluoride to be used as the starting compound in process (10) is the subject of German Patent Application P No. 2 915 738 [Le A 19 590].

This compound is obtained when 4-chloro-benzoyl chloride is converted into 4-fluoro-benzoyl fluoride by reaction with potassium fluoride and the 4-fluoro-benzoyl fluoride is brominated to give 3-bromo-4-fluoro-benzoyl fluoride, according to the equation below:

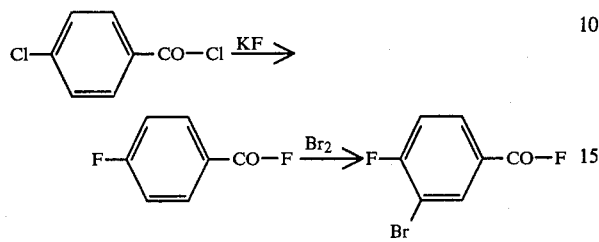

4-Chloro-benzoyl chloride is reacted with potassium fluoride, for example in tetramethylene sulphone, at temperatures between 200° and 220° C. and the reaction mixture is worked up by distillation. 4-Fluoro-benzoyl fluoride of boiling point 53° C./20 mbars. (refractive index: $n_D^{20} = 1.4792$) is obtained.

4-Fluoro-benzoyl fluoride is reacted with elementary bromine in the presence of 1% of iron (III) chloride at 70° to 75° C. In a batch of 1 mol, 40 g of unchanged starting material and 182 g of a mixture of 3-bromo-4-fluoro-benzoyl fluoride (boiling point: 82°–83° C./15 mbars; refractive index: $n_D^{20} = 1.5315$; melting point: 32°–34° C.) and 3-bromo-4-fluoro-benzoyl bromide (boiling point: 123° C./15 mbars; melting point: 35°–37° C.) remain after distillation.

PREPARATIVE EXAMPLES

Example 1

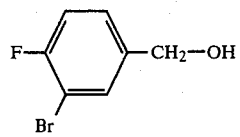

221 g (1 mol) of 3-bromo-4-fluoro-benzoyl fluoride were added dropwise to a mixture of 30.4 g (0.8 mol) of sodium tetrahydridoborate and 840 ml of isopropanol at 20°–25° C. in the course of 3 hours. The reaction mixture was stirred for about a further 30 minutes and then poured into 2 liters of ice-water. The pH was adjusted to 1 by adding concentrated hydrochloric acid, and the organic layer was then separated off. The aqueous phase was subsequently extracted with 200 ml of methylene chloride. The combined organic phases were dried and filtered and the filtrate was distilled. 163 g (79.5% of theory) of 3-bromo-4-fluoro-benzyl alcohol of boiling point 137° C./16 mbars and of refractive index $n_D^{20} = 1.5623$ were obtained.

EXAMPLE 2

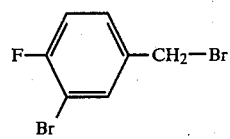

20.5 g (0.1 mol) of 3-bromo-4-fluoro-benzyl alcohol were dissolved in 100 ml of anhydrous toluene, and 10 g of phosphorus tribromide were added dropwise at 0° to 10° C., while stirring. The mixture was then stirred at room temperature for 2 hours. The reaction batch was subsequently poured into 500 ml of water, the organic phase was separated off and dried over magnesium sulphate and the solvent was distilled off under a water-pump vacuum. The residue was distilled in vacuo. 24 g (89.6% of theory) of 3-bromo-4-fluoro-benzyl bromide with a boiling point of 99°–100° C./3 mbars were obtained.

EXAMPLE 3

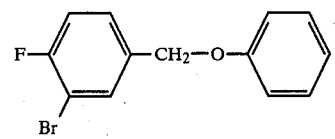

13.4 g (0.05 mol) of 3-bromo-4-fluoro-benzyl bromide were added dropwise to a suspension of 5.8 g (0.05 mol) of sodium phenolate in 100 ml of acetonitrile at 20°–25° C., while stirring. The mixture was then heated to 80° C. for 3 hours, while stirring. After cooling, the reaction batch was poured into 500 ml of water and extracted twice with 200 ml of methylene chloride each time. The organic phase was separated off and dried over magnesium sulphate and the solvent was stripped off under a waterpump vacuum. The residue was distilled in vacuo and 12.6 g (90% of theory) of 3-bromo-4-fluoro-benzyl phenyl ether with a boiling point of 145°–147° C./3 mbars were obtained.

EXAMPLE 4

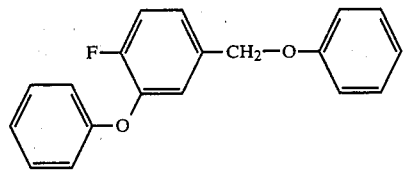

A mixture of 84.3 g (0.3 mol) of 3-bromo-4-fluorobenzyl phenyl ether, 34.8 g (0.3 mol) of sodium phenolate, 7 g (0.11 mol) of copper powder, 10 g of potassium chloride and 50 ml of bis-(2-methoxyethyl) ether (diglyme) was heated to 160° C. for 5 hours, while stirring. The reaction batch was then cooled to 80° C., 300 ml of toluene were added and the mixture was filtered. The filtrate was washed once with 100 ml of 10% strength sodium sulphate and was then extracted twice by shaking with 300 ml of water each time. The organic phase was dried over magnesium sulphate and the solvent was stripped off under a water-pump vacuum. The oily residue was distilled in vacuo. 70.7 g (80.2% of theory) of 4-fluoro-3-phenoxy-benzyl phenyl ether with the boiling point 195°–197° C./3 mbars were obtained as a very viscous oil.

EXAMPLE 5

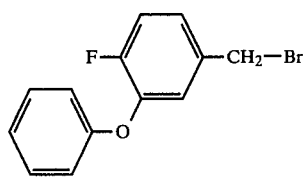

A mixture of 14.7 g (0.05 mol) of 4-fluoro-3-phenoxy-benzyl phenyl ether, 50 ml of 32% strength aqueous hydrobromic acid and 60 ml of glacial acetic acid was heated to the reflux temperature for 10 hours, while stirring. The reaction mixture was then poured into 200 ml of water and extracted twice with 200 ml of methylene chloride each time. The combined methylene chloride phases were then extracted twice by shaking with 100 ml of 10% strength sodium hydroxide solution each time. The organic phase was subsequently dried over magnesium sulphate and the solvent was then stripped off under a waterpump vacuum. The residue was freed from the last residues of solvent by incipient distillation at a bath temperature of 60° C./3 mbars. 4-Fluoro-3-phenoxy-benzyl bromide was thus obtained as a viscous oil.

EXAMPLE 6

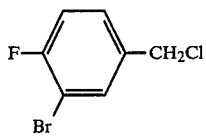

41 g (0.2 mol) of 3-bromo-4-fluoro-benzyl alcohol were dissolved in 250 ml of carbon tetrachloride, and 26 g of thionyl chloride were added dropwise at 20° C., while stirring. The mixture was then stirred at 25°–30° C. for 4 hours and the solvent and excess thionyl chloride were subsequently stripped off at 20° C. under a waterpump vacuum. The residue was distilled in vacuo. 29 g (64.9% of theory) of 3-bromo-4-fluoro-benzyl chloride with a boiling point of 85°–87° C./3 mbars were obtained.

EXAMPLE 7

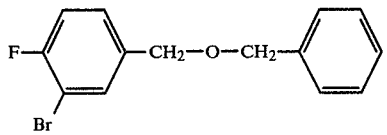

20.5 g (0.1 mol) of 3-bromo-4-fluoro-benzyl alcohol were added to a solution of 12.3 g (0.11 mol) of potassium tert.-butylate in 200 ml of tetrahydrofuran at 20° C. During this addition, the temperature increased to about 40° C. The mixture was subsequently stirred at 20° C. for about 1 hour and 12.6 g (0.1 mol) of benzyl chloride were then added dropwise to the reaction mixture. Thereafter, the mixture was heated under reflux for one hour. It was then cooled. About 200 ml of water and 50 ml of concentrated hydrochloric acid were added to the reaction mixture and the mixture was extracted twice with 200 ml of diethyl ether each time. The combined extracts were concentrated, dried over sodium sulphate and then subjected to fractional distillation. 14.2 g (48.2% of theory) of 3-bromo-4-fluoro-benzyl ether were obtained in the form of a light yellow oil of boiling point 165° C./7 mbars.

EXAMPLE 8

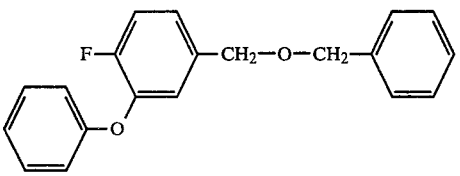

A mixture of 1 mol of 3-bromo-4-fluoro-benzyl benzyl ether, 1.1 mol of sodium phenolate, 0.12 mol of copper(I) oxide, 80 g of 4 MgCO$_3$.Mg(OH)$_2$.4 H$_2$O and 1,500 ml of isoquinoline was heated to 160° C. for 12 hours. The reaction mixture was then cooled, diluted with cyclohexane and filtered. The filtrate was washed with dilute hydrochloric acid and water, dried over sodium sulphate and filtered and the filtrate was distilled. 4-Fluoro-3-phenoxy-benzyl benzyl ether was obtained in the form of a yellow oil of boiling point 135° C./1 mbar in a yield of 75% of theory.

When the magnesium carbonate in Example 8 was replaced by 140 g of potassium carbonate and 0.2 mol of copper(I) oxide was used as the catalyst, the same product was obtained in a yield of 70% of theory in a reaction time of 8 hours.

It will be appreciated that the instant specification and examples are set forth by way of illustration and not limitation, and that various modifications and changes may be made without departing from the spirit and scope of the present invention.

We claim:

1. A 3-bromo-4-fluoro-benzyl derivative of the formula

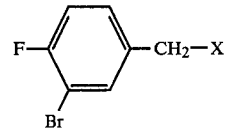

in which X is hydroxy, phenoxy, benzyloxy, chlorine or bromine.

2. A compound according to claim 1 in which X is phenoxy.

3. A compound according to claim 1 in which X is benzyloxy.

4. A compound according to claim 1, in which X is chlorine or bromine.

5. A process for preparing a compound according to claim 4, comprising reacting 3-bromo-4-fluoro-benzyl alcohol with a chlorinating or brominating agent at −10° to 100° C.

6. A compound according to claim 1 in which X is hydroxy.

7. A process for preparing the compound of claim 6, comprising reacting 3-bromo-4-fluoro-benzoyl fluoride with a complex hydride of the formula

M(M'H$_4$)

in which

M is lithium, sodium or potassium, and

M' is boron or aluminum, at about 0° to 50° C.

* * * * *